United States Patent [19]

Naito et al.

[11] 4,269,839

[45] May 26, 1981

[54] ALKYLTHIO-ADENINES USED AS BRONCHODILATORS

[75] Inventors: Takayuki Naito, Kawasaki; Susumu Nakagawa, Tokyo; Tetsuro Yamasaki; Taka-aki Okita, both of Ichikawa; Haruhiro Yamashita, Tokyo, all of Japan

[73] Assignee: Bristol-Myers Company, New York, N.Y.

[21] Appl. No.: 74,848

[22] Filed: Sep. 13, 1979

[51] Int. Cl.³ .............................................. A61K 31/52
[52] U.S. Cl. ..................................................... 424/253
[58] Field of Search ......................................... 424/253

[56] References Cited

U.S. PATENT DOCUMENTS

| | | | |
|---|---|---|---|
| 3,862,189 | 1/1975 | Schwender | 260/252 |
| 3,917,837 | 11/1975 | Lin et al. | 424/253 |
| 3,930,005 | 12/1975 | Wojnar et al. | 424/253 |
| 4,172,829 | 10/1979 | Nako et al. | 424/253 |

FOREIGN PATENT DOCUMENTS 1493684  11/1977  United Kingdom .

OTHER PUBLICATIONS

Kikugawa et al., Chem. Pharm. Bull., 25 (7), 1811–1821, (1977).
Japanese Published Application J5-2071-492, (Farmdoc 53190y).
Montgomery et al., J. Am. Chem. Soc., 80, 409–411, (1958).
Schaeffer et al., J. Am. Chem. Soc., 81, 197–201, (1959).

*Primary Examiner*—Leonard Schenkman
*Attorney, Agent, or Firm*—Robert H. Uloth; Robert E. Carnahan

[57] ABSTRACT

Adenine derivatives with 2-alkylthio and 9-(2-cyclohexenyl or cyclohexyl) substituents having non-adrenergic bronchodilating properties and use in the treatment or prophylaxis of broncho-constriction in mammals are disclosed.

3 Claims, No Drawings

ALKYLTHIO-ADENINES USED AS BRONCHODILATORS

BACKGROUND OF THE INVENTION

This invention broadly relates too heterocyclic carbon compounds having drug and bio-affecting properties and use thereof in a therapeutic process. In particular, the invention concerns 2-alkylthio-adenine derivatives having non-adrenergic smooth muscle relaxant properties making them particularly valuable in overcoming acute bronchospasm and as adjuncts in symptomatic management of chronic, obstructive pulmonary diseases (e.g., asthma, bronchitis, emphysema). Specifically, the invention is concerned with use of the 2-alkylthio-adenine derivatives in a bronchodilating process.

Regarding types of non-adrenergic bronchodilators, the theophylline groups of xanthine derivatives are particularly prominent. For instance, aminophylline, the ethylenediamine salt of theophylline, is an effective bronchodilator which may be administered parenterally, orally, or rectally and is useful in patients where direct relaxation of bronchial muscle is desired. Notwithstanding widespread use, the xanthine class of non-adrenergic bronchodilators have major disadvantages with respect to gastric irritation, cardiovascularand central nervous system side effects. Thus, there is a need for new and effective bronchodilators with increased potency and/or fewer or reduced untoward effects. As shown by standard pharmacological tests, representative compounds of the instant invention have non-adrenergic bronchodilating activity with minimal cardiovascular and central nervous system side effects.

Adenine is 6-aminopurine and purine contains a six-membered pyrimidine ring fused to the five-membered imidazole ring as shown in the following plane formula with the numbering system used herein noted.

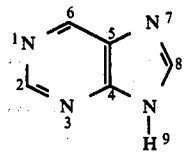

Various types of purine derivatives are known in which the parent substance purine is substituted at one or more of positions 2, 6, and 9 as illustrated in the following references.

1. K. Kikugawa, et al., Chem. Pharm. Bull., 25 (7), 1811–1821 (1977) describe synthesis of various 2-thioadenine derivatives of the formula

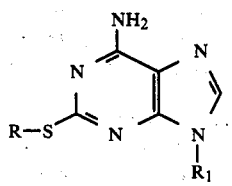

wherein inter alia R and $R_1$ are alkyl, cycloalkyl, etc., as platelet aggregation inhibitors. Specific examples of such compounds include those in which R is propyl or n-hexyl and $R_1$ is n-hexyl; R and $R_1$ are cyclopentyl. The authors concluded from the study that the ribosyl moiety of 2-thioadenosine derivatives was essential to the effective inhibition of platelet aggregation and could not be replaced by other substituents.

2. Japanese published application 52-71492 (Farmdoc 53190Y) discloses compounds of the formula

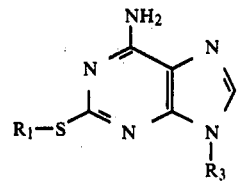

wherein $R_1$ is $C_1$—$C_{10}$ straight or branched alkyl, $C_5$—$C_{10}$ cycloalkyl, $C_7$—$C_{11}$ aralkyl or piperazinoethyl of the formula

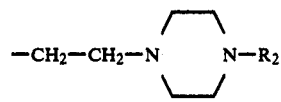

wherein $R_2$ is $C_7$—$C_{11}$ aralkyl, mono-substituted aralkyl, cinnamyl or fluorenyl; $R_3$ is $C_1$—$C_{10}$ straight or branched alkyl, $C_5$—$C_{10}$ cycloalkyl, $C_7$—$C_{11}$ aralkyl or piperazinoethyl as defined above, with the exclusion of compounds in which $R_1$ and $R_3$ are methyl, $R_1$ is methyl and $R_3$ is ethyl and $R_1$ is $C_5$—$C_{10}$ cycloalkyl and $R_3$ is $C_1$—$C_4$ alkyl, $C_5$—$C_{10}$ cycloalkyl or $C_7$—$C_{11}$ aralkyl. The compounds reportedly show an inhibitory effect on blood platelet aggregation and coronary dilating activity.

3. British Pat. No. 1,493,684 describes S-substituted 2-thioadenosines reportedly useful as platelet inhibitors and coronary vasodilators represented by the formula

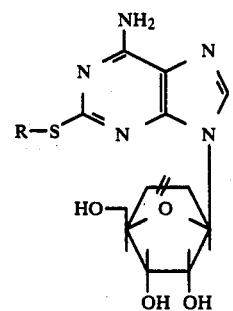

wherein inter alia R is $C_1$—$C_{10}$ straight or branched chain alkyl.

4. J. A. Montgomery, et al., J. Am. Chem. Soc., 80 409—411 (1958) describe adenine derivatives of the formula

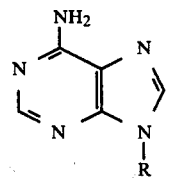

wherein R is n-butyl, cyclopentyl or cyclohexyl as potential anti-cancer agents.

5. H. J. Schaeffer, et al., J. Am. Chem. Soc., 81 197–201 (1959) describe synthesis of compounds having the formula

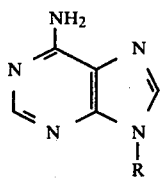

wherein R is 2-hydroxycyclohexyl or 2-cyclohexenyl as potential anti-cancer agents.

6. U.S. Pat. No. 3,917,837 (Lin, et al.) discloses the use of the compound

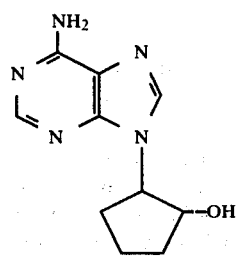

as an anti-inflammatory agent.

7. U.S. Pat. No. 3,862,189 (Schwender) concerns compounds of the formula

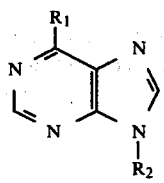

wherein inter alia, $R_1$ is amino, alkylamino, aralkylamino, etc.; and $R_2$ is di-substituted phenylalkyl, tetrahydroquinoylalkyl, etc. useful as antianginal or bronchodilator agents.

8. U.S. Pat. No. 3,930,005 (Wojnar, et al.) discloses compounds of the formula

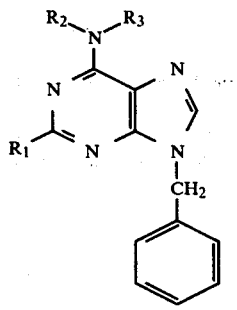

wherein $R_1$ is hydrogen, halogen, lower alkyl, lower alkoxy, amino, lower alkylamino or di-lower alkylamino and $R_2$ and $R_3$ may be hydrogen or lower alkyl as possessing anti-inflammatory activity.

9. Belgian Pat. No. 853,086 (Farmdoc 70719Y) discloses compounds of the formula

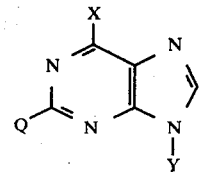

wherein either X is $C_1$—$C_6$ alkoxy or —NHR; R is H or (lower)alkyl; Y is $C_1$—$C_6$ alkyl, $C_3$—$C_{10}$ cycloalkyl or hydroxycycloalkyl, phenyl, halophenyl, trifluoromethyl-phenyl, bicycloalkyl or hydroxybicycloalkyl of up to 12 carbons, or —$AR^1$; A is methylene or ethylene; $R^1$ is phenyl, halophenyl, trifluoromethyl-phenyl, bicycloalkyl or hydroxybicycloalkyl of up to 12 carbons; Q is H, $C_1$—$C_6$ alkyl, $C_3$—$C_{10}$ cycloalkyl or hydroxycycloalkyl, bicycloalkyl or hydroxybicycloalkyl of up to 12 carbons, phenyl, halophenyl, trifluoromethyl-phenyl or $AR^1$; or X is halogen or (lower)dialkylamino; Y is methyl, ethyl cyclopentyl, phenyl, halophenyl, trifluoromethyl-phenyl or benzyl and Q is as previously defined. The compounds are reported to be useful in treating psoriasis.

SUMMARY AND DETAILED DESCRIPTION OF THE INVENTION

The 2-alkylthio-adenine derivatives of the instant invention are characterized by a compound of Formula I

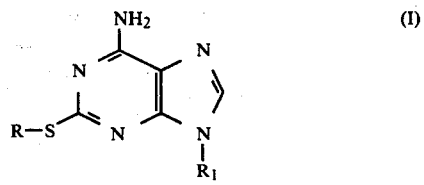

(I)

wherein R is lower alkyl of 1 to 4 carbon atoms; $R_1$ is cyclohexyl or 2-cyclohexenyl; or a pharmaceutically acceptable acid addition salt thereof. Said compounds effectively inhibit histamine induced bronchial constriction by acting directly on tracheal muscle to relax spasm and in this respect belong to the non-adrenergic class of bronchodilators.

It is to be understood that the term "lower alkyl" contemplates both stright and branched chain groups containing from 1 to 4 carbon atoms inclusive. Illustrative of such groups are methyl, ethyl, propyl, isopropyl, 1-butyl, 1-methylpropyl, 2-methylpropyl and tert.-butyl.

For the purpose of this disclosure, the term "pharmaceutically acceptable" acid addition salt denotes a salt form of a compound of Formula I obtained by combination with a non-toxic inorganic or organic acid which is relatively non-toxic in anionic form. Examples of non-toxic pharmeceutically acceptable acid addition salts of the compounds of Formula I are those formed with sulfuric, hydrochloric, phosphoric, hydrobromic, hydroiodic, sulfamic, methanesulfonic, benzenesulfonic, para-toluenesulfonic, acetic, lactic, succinic, malic, maleic, mucic, tartaric, citric, gluconic, benzoic, cinnamic, isethionic, furmaric, levulinic and related acids.

Conversion of Formula I compounds to corresponding non-toxic pharmaceutically acceptable acid addition salt is accomplished in conventional fashion by admixture of the base with at least one molecular equivalent of a selected acid in an inert organic solvent such as ethanol, benzene, ethyl acetate, ether halogenated hydrocarbon and the like. Isolation of the salt is carried out by techniques known to the art such as inducing precipitation with a non-polar solvent (e.g. ether) in which the salt has limited solubility.

According to the present invention, compounds of Formula I are prepared by processes illustrated in the following reaction scheme:

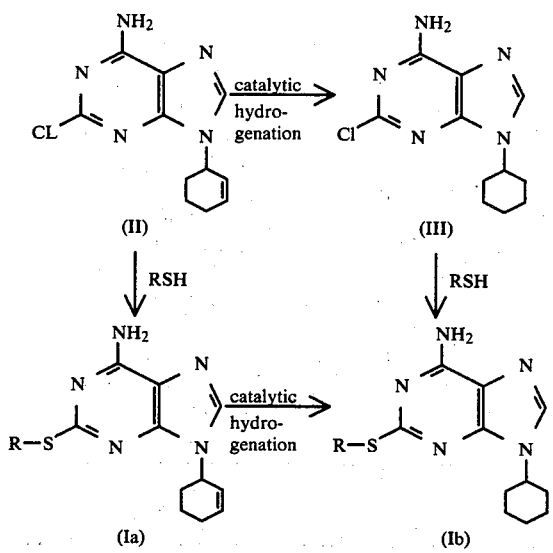

As set forth herein, Formula (I) compounds are obtained by reacting 2-chloro-9-(2-cyclohexenyl)-9H-adenine (II) or 2-chloro-9-cyclohexyl-9H-adenine (III) with an alkali metal mercaptide of the formula RS-alk wherein alk represents sodium, potassium or lithium and R is as defined above in an inert solvent until the desired free base Formula (I) product is formed and converting said product, if desired, to a phramaceutically acceptable acid addition salt thereof by conventional methods illustrated herein. The required alkali metal mercaptides "RS-alk" are conveniently obtained by treating the mercaptan with alkali metal hydroxides (e.g. sodium or potassium hydroxide) or preferably alkali metal hydrides (e.g., sodium or potassium hydride) in an inert solvent. As used herein, the term "inert solvent" refers to any solvent (e.g. dimethylformamide) chemically inert to the 2-chloroadenine starting materials (II) and (III) or the RS-alk mercaptides. Elevated temperatures ranging from about 50° C. to 150° C. are preferably employed in the reaction which is carried out for a time period ranging from 0.5 to 24 hrs.

Formula (I) compounds wherein $R_1$ is cyclohexyl (i.e. Ib) are also conveniently prepared by catalytic hydrogenation of the corresponding Formula (Ia) products. As an example of a suitable procedure, a compound of Formula (Ia) is dissolved in a suitable nonreducible, inert solvent (e.g. methanol, ethanol, water, aqueous methanol, aqueous ethanol) and then hydrogenated using a conventional hydrogenation catalyst. Examples suitable catalysts include palladium black, Pd-BaSO$_4$, Pd-C, PtO$_2$, Ru-C, Raney nickel, CuCrO, RhCl[P(C$_6$H$_5$)$_3$]$_3$ and RuCl[P(C$_6$H$_5$)$_3$]$_3$. A preferred catalyst is palladium-on-carbon. While temperature and pressure are not critical for the hydrogenation step, advantageous results have been achieved under conditions of room temperature and atmospheric pressure.

The requisite 2-chloro-9-(2-cyclohexenyl)-9H-adenine (II) and 2-chloro-9-cyclohexyl-9H-adenine (III) starting materials are obtained as described in allowed U.S. Patent application Ser. No. 904,146 (issued Oct. 30, 1979 as U.S. Pat. No. 4,172,829) incorporated herein in its entirety be reference.

According to the present invention, a compound identified by Formula I or a pharmaceutically acceptable salt thereof is useful in a process for eliciting a bronchodilating effect in a mammal in need thereof which comprises systemic administration to said mammal an effective dose of from about 0.1 to 20 mg./kg. body weight of the Formula I compound. A particularly preferred compound for carrying out the process is 9-(2-cyclohexenyl)-2-n-propylthio-9H-adenine. It is intended by systemic administration to include both oral and parenteral routes, e.g., intramusclar, intravenous, intraperitoneal and subcutaneous. Also, the active ingredient may be given by inhalation employing a suitable aerosol preparation. Oral administration is preferred.

Another aspect the present invention provides a pharmaceutical composition in dosage unit form useful for relief of bronchial constriction in mammals. The composition comprises, as the active ingredient, an effective bronchodilating amount of a compound of Formula I or a pharmaceutically acceptable acid addition salt thereof, in admixture with a pharmaceutically acceptable carrier or diluent.

The pharmacologically active compounds of the present invention may be administered either as individual therapeutic agents or as mixtures with other therapeutic agents. They may be administered alone, but are generally given in the form of pharmaceutical compositions. Examples of such compositions include tablets, lozenges, capsules, powders, aerosol sprays, aqueous or oily suspensions, syrups, elixirs, and aqueous solutions.

The nature of the pharmaceutical composition and the pharmaceutical carrier or diluent will, of course, depend on the desired route of administration. For example, oral compositions may be in form of tablets or capsules and may contain conventional excipients such as binding agents (e.g. syrup, acacia, gelatin, sorbitol, tragacanth or polyvinylpyrrolidone), fillers (e.g. lactose, sugar, maize-starch, calcium phosphate, sorbitol or glycine), lubricants (e.g. magnesium stearate, talc, polyethylene glycol or silica), disintegrants (e.g. starch) or wetting agents (e.g. sodium lauryl sulfate). Oral liquid preparations may be in the form of aqueous or oily suspensions, solutions, emulsions, syrups, elixirs, etc. or may be presented as a dry product for reconstitution with water or other suitable vehicle before use. Such liquid preparations may contain conventional additives such as suspending agents, flavoring agents, diluents or emulsifying agents. For parenteral administration or inhalation, solutions or suspensions of a compound of Formula I with conventional pharmaceutical vehicles may be employed, e.g. as an aerosol spray for inhalation, as an aqueous solution for intravenous injection or as an oily suspension for intramuscular injection.

The compounds pharmaceutical compositions and broncho-dilating use thereof constituting embodiments of this invention are more fully illustrated by the following examples.

EXAMPLE 1

9-(2-Cyclohexenyl)-2-n-propylthio-9H-adenine

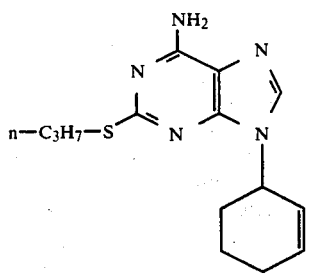

A mixture of 2-chloro-9-(2-cyclohexenyl)-9H-adenine (159 mg., 0.64 mmole), 50% sodium hydride (223 mg., 4.65 mmole) and 2 ml. of n-propyl mercaptan in 10 ml. of N,N-dimethylformamide is refluxed for a 5 hr. period under nitrogen and then poured into ice water and neutralized with 1 N HCl. Excess mercaptan is removed by evaporation under reduced pressure and residual solution extracted with chloroform which is then washed with water, dried over $Na_2SO_4$ and filtered. The filtrate is evaporated and residual material purified by silica gel chromatography (5 g) using 1% $MeOH-CHCl_3$ as eluant to provide 167 mg. (90%) of 9-(2-cyclohexenyl)-2-n-propylthio-9H-adenine, m.p. 108°–113° C. IR(KRr): 3310, 3150, 2920, 1655, 1585, 1450, 1320, 1240 cm$^{-1}$. UV:$\lambda_{max}^{EtOH}$ 237 nm($\epsilon$23,300), 278 nm($\epsilon$13,750). NMR(CDCl$_3$):$\delta$1.01(3H,t, J=7Hz), 1.90(8H,m), 3.07(2H,t, J=7Hz), 5.10(1H,m), 5.82(2H,s), 5.92(2H,m), 7.60(1H,s).

Anal. Calcd. for $C_{14}H_{19}N_5S$: C, 58.10; H, 6.62; N, 24.20; S, 11.08. Found: C, 57.90; H, 7.01; N, 23.90; S, 11.41.

EXAMPLE 2

9-Cyclohexyl-2-n-propylthio-9H-adenine

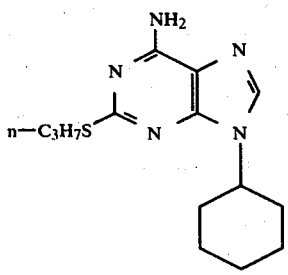

A mixture of 2-Chloro-9-cyclohexyl-9H-adenine (136 mg., 0.54 mmole), 2.3 ml. of n-propyl mercaptan and sodium hydride (220 mg., 4.5 mmole) in 12 ml. of N,N-dimethylformamide is gently refluxed for a 2.5 hr. period. After cooling, the mixture is neutralized with 1 N HCl and evaporated to remove excess mercaptan. Residual material is shaken with chloroform and water and the organic layer washed with water, dried over sodium sulfate and evaporated in vacuo to leave an oil. Purificatin of the oily residue is carried out by chromatography on silica gel using $MeOH-CHCl_3$ (1:99) to afford material which crystallized from cyclohexane to afford 112 mg. (70%) of 9-cyclohexyl-2-n-propylthio-9H-adenine as colorless prisms, m.p. 140°–150° C. IR(KBr): 3300, 3120, 2920, 1650, 1585, 1435, 1305, 1220cm.$^{-1}$. UV:- $\lambda_{max}^{EtOH}$ 237 nm($\epsilon$23,900), 278 nm($\epsilon$13,800). NMR(CDCl$_3$):$\delta$1.06(3H,t,J=7Hz), 1.80(12H,m), 3.14(2H,t,J=7Hz), 6.07(2H,s), 7.70(1H,s).

Anal. Cacld. for $C_{14}H_{21}N_5S$: C, 58.10; H, 6.62; N, 24.20; S, 11.08. Found: C, 58.07; H, 7.27; N, 23.98; S, 10.83.

An alternate procedure for preparing the title compound employs the product of Example 1 as starting material. Thus, catalytic hydrogenation of 9-(2-cyclohexenyl)-2-n-propylthio-9H-adenine in ethanol with 10% palladium-on-charcoal affords 9-cyclohexyl-2-n-propylthio-9H-adenine.

EXAMPLE 3

Pharmacological Evaluation

A. In Vitro Bronchodilator Activity.

Tracheal chains of guinea pig were prepared by the method of A. Akcasu, Arch. Int. Pharmcodyn. Ther., 122, 201 (1959). The response to each test compound was recorded by the Magnus method and expressed as a percentage of the maximum response obtained with 0.1 mcg./ml. of isoproterenol prior to each experiment. Bronchodilator activity (in vitro) of aminophylline and test compounds of Example 1-2 is expressed below as an $EC_{50}$ value (concentration in mcg./ml. which produces a relaxation which is 50% of the maximum response to 0.1 mcg./ml. of isoproterenol).

| In Vitro Test Results | |
|---|---|
| Compound of Example | $EC_{50}$ (mcg./ml.) |
| 1 | 0.02 |
| 2 | 0.19 |
| Aminophylline | 16.6 |

B. In Vivo Bronchodilator and Hypotensive Activity.

The in vivo bronchodilator activity of aminophylline and test compounds was evaluated according to a modification of the method described by L. G. W. James, J. Pharm. Pharmac., 21, 379 (1969) by measuring decrease in intratracheal pressure (ITP) in the guinea pig. The trachea of anesthetized guinea pig was cannulated and the ITP recorded on a polygraph under artificial ventilation. Arterial blood pressure (ABP; reflecting hypotensive activity) was also measured during the experiment. Either intravenous or intraduodenal routes of administration are used. Results set forth below express the broncho-dilator activity (ITP) as an $ED_{50}$ value (dose in mg./kg. resulting in a 50% decrease in intratracheal pressure) and the hypotensive activity (ABP) as an $ED_{20}$ value (dose in mg./kg. which reduces arterial blood pressure by 20%). The ratio of hypotensive $ED_{20}$/bronchodilating $ED_{50}$ reflects an assessment of the separation of desirable bronchodilator activity from undesirable cardiovascular (hypotensive) effect in the compounds. Those compounds exhibiting the largest ABP/ITP ratios have the greatest separation of bronchodilator activity and hypotensive side effect.

| | Intravenous Test Results | | Ratio |
|---|---|---|---|
| Compound of | (mg./kg.) | | |
| Examples | ITP $ED_{50}$ | ABP $ED_{20}$ | ABP/ITP |
| 1 | 0.31 | >3 | >9.7 |
| 2 | 1.1 | >3 | >2.7 |

| Compound of Examples | Intravenous Test Results (mg./kg.) | | Ratio ABP/ITP |
|---|---|---|---|
| | ITP ED$_{50}$ | ABP ED$_{20}$ | |
| Aminophylline | 0.58 | 1.4 | 2.4 |

EXAMPLE 4

Pharmaceutical Compositions

A. Tablets.

The compounds of Formula I are compounded into tablets according to the following example:

| Materials | Amount |
|---|---|
| 9-(2-Cyclohexenyl)-2-n-prpopylthio-9H-adenine | 20.0 g. |
| Magnesium stearate | 1.3 g. |
| Corn starch | 12.4 g. |
| Corn starch, pregelatinized | 1.3 g. |
| Lactose | 215.0 g. |

The foregoing materials are blended in a twin-shell blender and then granulated and pressed into tablets employing 250 mg. each. Each tablet contains about 20 mg. of active ingredient. The tablets may be scored and quartered so that unit doses of 5.0 mg. of active ingredient may be conveniently obtained.

B. Capsules.

The purine derivatives of Formula I are compounded into capsules according to the following example:

| Materials | Amount |
|---|---|
| 9-(2-Cyclohexenyl)-2-n-propylthio-9H-adenine | 50.0 g. |
| Lactose | 221.0 g. |
| Magnesium stearate | 4.0 g. |

The foregoing materials are blended in a twin-shell blender and No. 1 hard gelatin capsules filled with 275 mg. of the blended compositon. Each capsule contains 50 mg. of active ingredient.

What is claimed is:

1. A bronchodilating process which comprises systemic administration to a mammal in need thereof an effective dose of from about 0.1 to 20 mg./kg. body weight of a compound of Formula I

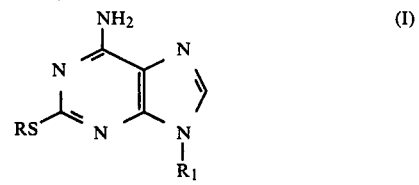

wherein

R is lower alkyl of 1 to 4 carbon atoms inclusive;

R$_1$ is cyclohexyl or 2-cyclohexenyl;

or a pharmaceutically acceptable acid addition salt thereof.

2. The method as claimed in claim 1 wherein the active ingredient is 9-(2-cyclohexenyl)-2-n-npropylthio-9H-adenine or a pharmaceutically acceptable acid addition salt thereof.

3. The method as claimed in claim 2 wherein the active ingredient is 9-cyclohexyl-2-n-propylthio-9H-adenine or a pharmaceutically acceptable acid addition salt thereof.

* * * * *